United States Patent
Nakahara et al.

(10) Patent No.: US 10,111,920 B2
(45) Date of Patent: Oct. 30, 2018

(54) SALT-FREE MISO PRODUCTION METHOD, SALT-FREE MISO, HEPATIC FUNCTION IMPROVEMENT AGENT, AND HYPERTENSION IMPROVEMENT AGENT

(71) Applicants: MARUZEN PHARMACEUTICALS CO., LTD., Onomichi-shi, Hiroshima (JP); MASUYAMISO CO., LTD., Kure-shi, Hiroshima (JP)

(72) Inventors: Tatsuo Nakahara, Fukuyama (JP); Takashi Kawano, Kure (JP)

(73) Assignees: MARUZEN PHARMACEUTICALS CO., LTD., Onomichi-Shi (JP); MASUYAMISO CO., LTD., Kure-Shi (JP)

( * ) Notice: Subject to any disclaimer, the term of this patent is extended or adjusted under 35 U.S.C. 154(b) by 26 days.

(21) Appl. No.: 15/128,742

(22) PCT Filed: Jan. 6, 2015

(86) PCT No.: PCT/JP2015/050103
§ 371 (c)(1),
(2) Date: Sep. 23, 2016

(87) PCT Pub. No.: WO2015/146206
PCT Pub. Date: Oct. 1, 2015

(65) Prior Publication Data
US 2017/0100444 A1 Apr. 13, 2017

(30) Foreign Application Priority Data
Mar. 26, 2014 (JP) ................................ 2014-063950

(51) Int. Cl.
| | | |
|---|---|---|
| A61K 36/00 | (2006.01) | |
| A61K 36/48 | (2006.01) | |
| A61K 36/062 | (2006.01) | |
| A23L 11/00 | (2016.01) | |
| A23L 33/10 | (2016.01) | |
| A61K 9/00 | (2006.01) | |

(52) U.S. Cl.
CPC ............. *A61K 36/48* (2013.01); *A23L 11/09* (2016.08); *A23L 33/10* (2016.08); *A61K 9/0056* (2013.01); *A61K 36/062* (2013.01); *A23V 2002/00* (2013.01); *A61K 2236/11* (2013.01); *A61K 2236/19* (2013.01)

(58) Field of Classification Search
CPC .................................................. A61K 36/00
See application file for complete search history.

(56) References Cited

U.S. PATENT DOCUMENTS 6,045,819 A    4/2000  Takebe
2008/0160117 A1*  7/2008  Koyama ............... A23L 3/3571
                                                          424/757

FOREIGN PATENT DOCUMENTS

| CN | 102485031 A | 6/2012 |
|---|---|---|
| JP | 64-4743 A | 1/1989 |
| JP | 2002-161045 A | 6/2002 |
| JP | 2006-70015 A | 3/2006 |
| JP | 2006-296255 A | 11/2006 |
| JP | 2007-6834 A | 1/2007 |
| JP | 2008-88151 A | 4/2008 |
| JP | 2008228654 A * | 10/2008 |
| JP | 2000-270799 A | 8/2012 |
| WO | WO 97/37549 A1 | 0/1997 |

OTHER PUBLICATIONS

Ak, T and M. Ak, "Soybean—a consummate functional food: A review," J. Food Sci. Technol (2005), vol. 42, No. 2, pp. 111-119.
Extended European Search Report dated Oct. 20, 2017, in European Patent Application No. 15770313.3.
Watanabe, H., "Beneficial Biological Effects of Miso with Reference to Radiation Injury, Cancer and Hypertension," J. Toxicol. Pathol. (2013), vol. 26, pp. 91-103.
Ishihara et al., "The outstanding effects of miso on general well being and health: The reduction in toxicity of burned meat and fish coated with miso before cooking [misozuke]: The preventive effect of miso on Trp-P-2-induced liver injury in mice", Miso Science and Technology, 2009, vol. 57, No. 2, pp. 55-66.
Iwashita et al., "Physiological Functions of Miso", Journal of the Brewing Society of Japan, 1994, vol. 89, No. 11, pp. 869-872.
Nakahara, "To Develop New Food Ingredients by Pressure Enzyme Decomposing Device", Food Processing and Ingredients, 2013, vol. 48, No. 12, pp. 74-75.
Watanabe, "Biological efficacies of Miso", Journal of the Brewing Society of Japan, 2010, vol. 105, No. 11, pp. 714-723.
International Search Report for PCT/JP2015/050103 (PCT/ISA/210) dated Apr. 14, 2015.
Written Opinion of the International Searching Authority for PCT/JP2015/050103 (PCT/ISA/237) dated Apr. 14, 2015.

* cited by examiner

*Primary Examiner* — Qiuwen Mi
(74) *Attorney, Agent, or Firm* — Birch, Stewart, Kolasch & Birch, LLP

(57) ABSTRACT

Provided are: a production method for salt-free miso, in which steamed soy beans and koji are pressurized, heated, and fermented; salt-free miso obtained by said production method; and a hepatic function improvement agent and a hypertension improvement agent that contain said salt-free miso as an effective component thereof.

1 Claim, 4 Drawing Sheets

SALT-FREE MISO PRODUCTION METHOD, SALT-FREE MISO, HEPATIC FUNCTION IMPROVEMENT AGENT, AND HYPERTENSION IMPROVEMENT AGENT

TECHNICAL FIELD

This invention relates to a method of producing salt-free miso having a good taste and flavor, which method also is capable of shortening the production process, and to salt-free miso. The invention additionally relates to a hepatic function-improving agent and to a hypertension-ameliorating agent.

BACKGROUND ART

Miso is known to take a long time to produce. Lately, given the trends toward shorter working hours and increased vacation time, there has been a desire for the development of an efficient method of making miso at the production site. The largest bottleneck in developing an efficient method of production without having to invest in plant and equipment is the fermentation step. Shortening the length of the fermentation step has a large effect on all the operations in that it shortens the production time. Conventional fermentation operations are carried out over an extended period of time at a low temperature so as not to deactivate the koji (*Aspergillus oryzae*). Because the production process is long, common salt or alcohol is often added to prevent other types of microorganisms from growing during the production process.

Consuming a large amount of salt-containing miso is regarded as one cause of the onset of hypertension. Hence, there exists a desire for miso that contains a reduced amount of salt. Low-salt miso to which alcohol has been added is known for this reason, yet salt-free miso has not seen practical application. Although salt-free miso is good for the health, it leaves something to be desired in terms of taste and flavor (soy flavor) and so has not been to the consumer's liking.

PRIOR ART DOCUMENTS

Patent Documents

Patent Document 1: JP-A S64-4743

SUMMARY OF THE INVENTION

Problems to be Solved by the Invention

In light of the above circumstances, one object of the invention is to provide a method of producing salt-free miso that can shorten the production process. Another object is to provide salt-free miso having a good taste and flavor that is produced by such a method. Further objects are to provide a hepatic function-improving agent and a hypertension-ameliorating agent that use this salt-free miso.

Means for Solving the Problems

The inventors have conducted extensive investigations, as a result of which they have discovered that by using steamed soybeans as the starting material and reacting the steamed soybeans with koji culture under applied heat and pressure, salt-free miso having a good taste and flavor can be obtained, in addition to which the production process can be shortened. The inventors have found that the resulting salt-free miso has an excellent hepatic function-improving effect and excellent hypertension-ameliorating and preventing effects.

Accordingly, the invention provides the following method of producing salt-free miso, the following salt-free miso, and the following hepatic function-improving agent and hypertension-ameliorating agent.

[1] A method of producing salt-free miso, comprising the step of fermenting steamed soybeans and koji culture under applied heat and pressure.

[2] The production method of [1], wherein the applied heat and pressure conditions are a pressure of 40 to 100 MPa and a temperature of 40 to 70° C.

[3] A salt-free miso obtained by the production method of [1] or [2].

[4] A hepatic function-improving agent comprising, as an active ingredient, the salt-free miso of [3].

[5] A hypertension-ameliorating agent comprising, as an active ingredient, the salt-free miso of [3].

[6] A method of improving hepatic function by administering the salt-free miso of [3] in a human.

[7] A method of ameliorating or preventing hypertension by administering the salt-free miso of [3] in a human.

The salt-free miso of [3] for use in a pharmaceutical product.

[8] The salt-free miso of [3] for use in a hepatic function-improving drug.

[9] The salt-free miso of [3] for use in a hypertension-ameliorating drug or prophylactic.

[10] The salt-free miso of [3] for use in manufacturing a pharmaceutical product for improving hepatic function.

[11] The salt-free miso of [3] for use in manufacturing a pharmaceutical product for ameliorating or preventing hypertension.

The production method of the invention enables salt-free miso having a good taste and flavor to be obtained, and moreover is able to shorten the production process. In addition, this production method enables an excellent hepatic function-improving agent and an excellent hypertension-ameliorating agent to be provided.

BRIEF DESCRIPTION OF DIAGRAMS

EMBODIMENT FOR CARRYING OUT THE INVENTION

Figure 1:
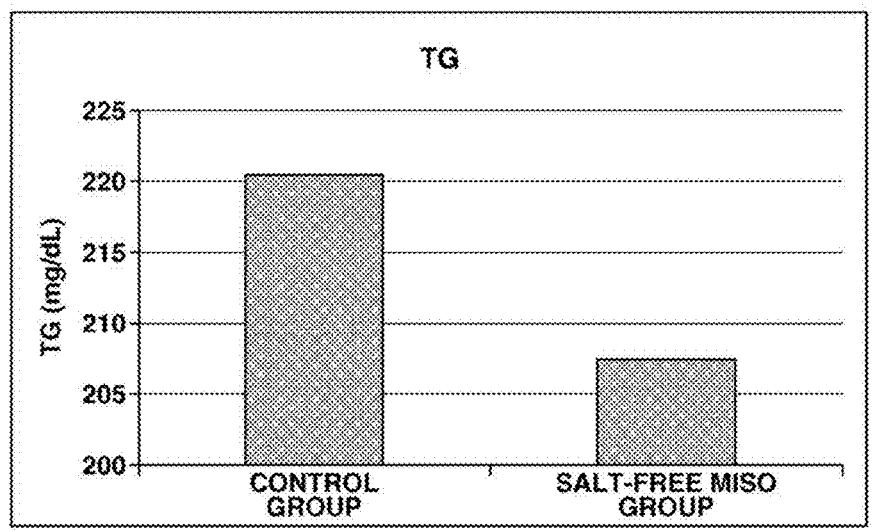
FIG. 1 is a graph showing the triglyceride (TG) results in Trial Example 1.

The salt-free miso production method of the invention involves reacting steamed soybeans with koji culture under applied heat and pressure. Miso is generally defined as a product containing soybeans, koji culture and salt. In this invention, "salt-free miso" refers to a product which contains soybeans and koji culture but does not contain salt; contains soybeans and koji culture.

[Steamed Soybeans]

Steamed soybeans serve as a starting material in the production method of the invention. When boiled soybeans are used, a loss of flavor occurs and so the good flavor intended is not obtained. The soybeans are not particularly limited; use may be made of commonly sold soybeans.

The soybeans are soaked in water before being steamed. Soaking is not particularly limited, so long as sufficient water is contained within the soybeans. Soaking should be carried out by completely immersing the soybeans in water and soaking them at a temperature of 10 to 30° C. for 5 to 20 hours, and preferably 10 to 12 hours.

The method of steaming is not particularly limited. Steamed soybeans may be obtained by using a steamer to steam the soybeans for 0.5 to 2 hours.

[Reacting Steamed Soybeans with Koji Culture Under Applied Heat and Pressure (Fermentation Step)]

In the practice of the invention, it is important for the reaction of steamed soybeans with koji culture to be carried out under applied heat and pressure. When the soybeans are subjected to heat and pressure before the fermentation step or are subjected to heat and pressure after the fermentation step, unlike in this invention, the length of the production process cannot be shortened and salt-free miso having a good taste and flavor is not obtained.

It is preferable to process the steamed soybeans before the fermentation step. A known apparatus such as a mixer or chopper may be used for this purpose. The processing time, etc. may be selected as appropriate, although processing to a minced or other state in which pieces of the steamed soybeans remain after processing is desirable.

The applied heat and pressure conditions include a pressure of preferably 40 to 100 MPa, and more preferably 50 to 80 MPa. Alternatively, the pressure may be set to from 50 to 70 MPa. The temperature is preferably from 40 to 70° C., and more preferably from 50 to 60° C. By thus adjusting the pressure and temperature in the fermentation step, this step can be made to proceed without deactivating the koji, resulting in a salt-free miso having a good taste and flavor and also enabling the production process to be shortened.

The koji (*A. oryzae*) is not particularly limited. Exemplary koji cultures include those obtained from grains such as rice or wheat or from beans. One such koji culture may be used alone, or two or more may be suitably selected and used together.

Although this invention enables the fermentation step to be shortened, the length of the fermentation step is preferably at least one day and may be at least two days or at least three days, with a period of one to five days being more preferred. Setting this period to at least one day allows the reaction to proceed to a sufficient degree. However, when the length of this step exceeds seven days, the miso may turn brown.

[Salt-Free Miso]

Because this production method enables salt-free miso having a good taste and flavor to be obtained without adding salt, and moreover contains no harmful microorganisms, there is no need to include salt or ethanol for the sake of preservation. The amount of salt included in the miso may be suitably set according to consumer preferences or the miso may be free of added salt.

[Hepatic Function-Improving Agent]

The deterioration of hepatic function is divided into conditions caused largely by alcohol and conditions not caused by alcohol. The indicators of improvement in hepatic function when deterioration in hepatic function is not attributable to alcohol are the hepatic function-related substances GOT and GPT. Deterioration in hepatic function due to decreased sugar metabolism and decreased fat metabolism is also known. The salt-free miso of the invention, as demonstrated in the subsequently described working examples, has been confirmed to have triglyceride-lowering, cholesterol-lowering, glucose-lowering and GPT-lowering effects and to maintain the liver weight when on a high-fat diet, and therefore is effective as a hepatic function-improving agent.

When the salt-free miso is used as a hepatic function-improving agent, the amount taken daily by one adult is preferably from 0.01 to 10 g, and more preferably from 0.1 to 5 g. The advantageous effects are better exhibited when taken in this range. To provide the above daily intake, the amount of salt-free miso included in the hepatic function-improving agent is suitably set within the range of 0.1 to 10 wt %.

The hepatic function-improving agent of the invention can be prepared as, for example, a nutraceutical, a specially designated health food, a quasi-drug, or a pharmaceutical preparation. The method in which it is taken (administered) is not particularly limited, and may be, for example, internal (e.g., oral) or external. Oral intake is preferred. The manner of use is not particularly limited; for example, this agent may be taken before or after meals or before going to bed. The dosage form is not particularly limited, and includes internal preparations such as granules, micropellets, powders, tablets, capsules, solutions, emulsions and suspensions; and external preparations such as lotions, ointments and poultices. The hepatic function-improving agent of the invention may include ordinary amounts of any ingredients commonly used in such agents, insofar as doing so does not detract from the advantageous effects of the invention.

[Hypertension-Ameliorating Agent]

The salt-free miso of the invention, as demonstrated in the subsequently described working examples, is effective as a hypertension-ameliorating agent. In addition to ameliorating hypertension, the hypertension-ameliorating agent of the invention can also be used for the prevention of hypertension.

When the salt-free miso is used as a hypertension-ameliorating agent, the amount taken daily by one adult is preferably from 0.01 to 10 g, and more preferably from 0.1 to 5 g. The advantageous effects are better exhibited when taken in this range. To provide the above daily intake, the amount of salt-free miso included in the hypertension-ameliorating agent is suitably set within the range of 0.1 to 10 wt %.

The hypertension-ameliorating agent of the invention can be prepared as, for example, a nutraceutical, a specially designated health food, a quasi-drug, or a pharmaceutical preparation. The method in which it is taken (administered) is not particularly limited, and may be, for example, internal (e.g., oral) or external. Oral intake is preferred. The manner of use is not particularly limited; for example, this agent may be taken before or after meals or before going to bed. The dosage form is not particularly limited, and includes internal preparations such as granules, micropellets, powders, tablets, capsules, solutions, emulsions and suspensions; and external preparations such as lotions, ointments and poultices. The hypertension-ameliorating agent of the invention may include ordinary amounts of any ingredients commonly used in such agents, insofar as doing so does not detract from the advantageous effects of the invention.

EXAMPLES

Working Examples, Comparative Examples and Trial Examples are given below to more concretely illustrate the invention, although the invention is not limited by these Examples.

Example 1

Water was added to 500 g of soybeans so as to completely immerse them, and the beans were soaked overnight at room temperature (20° C.). The soaked beans were then steamed for one hour in a steamer, and the resulting steamed soybeans were processed with a chopper into a minced form containing bean pieces. To this was added a rice koji culture in a soybean to rice koji ratio of 1:1 (dry weight basis; the same applies below), and treatment under applied heat and pressure at 50° C. and 60 MPa was carried out for five days.

The resulting salt-free miso was placed within a vessel in an amount normally used to prepare miso soup, and table salt was added to a salt concentration in the miso soup of 0.8 wt %. This miso soup was compared with a comparative miso soup (adjusted to a salt concentration of 0.8 wt %) prepared using commercial miso (Masuya Miso KK). As a result, a taste comparable to that of the comparative miso soup was obtained and the flavor was better than that of the comparative miso soup. Hence, the salt-free miso clearly was perfectly satisfactory as a miso.

Example 2

Water was added to 500 g of soybeans so as to completely immerse them, and the beans were soaked overnight at room temperature (20° C.). The soaked beans were then steamed for one hour in a steamer, and the resulting steamed soybeans were processed with a chopper into a minced form containing bean pieces. To this was added a rice koji culture in a soybean to rice koji ratio of 1:5, and treatment under applied heat and pressure at 50° C. and 60 MPa was carried out for five days. Evaluation was carried out in the same way as in Working Example 1, as a result of which a taste comparable to that of the comparative miso soup was obtained and the flavor was better than that of the comparative miso soup. Hence, the salt-free miso clearly was perfectly satisfactory as a miso. Moreover, the rice koji taste was stronger than in Working Example 1.

Example 3

Water was added to 500 g of soybeans so as to completely immerse them, and the beans were soaked overnight at room temperature (20° C.). The soaked beans were then steamed for one hour in a steamer, and the resulting steamed soybeans were processed with a chopper into a minced form containing bean pieces. To this was added a rice koji culture in a soybean to rice koji ratio of 1:1, and treatment under applied heat and pressure at 50° C. and 60 MPa was carried out for two days. Evaluation was carried out in the same way as in Working Example 1, as a result of which a taste comparable to that of the comparative miso soup was obtained and the flavor was better than that of the comparative miso soup. Hence, the salt-free miso clearly was perfectly satisfactory as a miso.

Example 4

Water was added to 500 g of soybeans so as to completely immerse them, and the beans were soaked overnight at room temperature (20° C.). The soaked beans were then steamed for one hour in a steamer, and the resulting steamed soybeans were processed with a chopper into a minced form containing bean pieces. To this was added a rice koji culture in a soybean to rice koji ratio of 1:1, and treatment under applied heat and pressure at 50° C. and 70 MPa was carried out for two days. Evaluation was carried out in the same way as in Working Example 1, as a result of which a taste comparable to that of the comparative miso soup was obtained and the flavor was better than that of the comparative miso soup. Hence, the salt-free miso clearly was perfectly satisfactory as a miso.

Example 5

Water was added to 500 g of soybeans so as to completely immerse them, and the beans were soaked overnight at room temperature (20° C.). The soaked beans were then steamed for one hour in a steamer, and the resulting steamed soybeans were processed with a chopper into a minced form containing bean pieces. To this was added a rice koji culture in a soybean to rice koji ratio of 1:1, and treatment under applied heat and pressure at 50° C. and 50 MPa was carried out for two days. Evaluation was carried out in the same way as in Working Example 1, as a result of which a taste comparable to that of the comparative miso soup was obtained and the flavor was better than that of the comparative miso soup. Hence, the salt-free miso clearly was perfectly satisfactory as a miso.

Example 6

Water was added to 500 g of soybeans so as to completely immerse them, and the beans were soaked overnight at room temperature (20° C.). The soaked beans were then steamed for one hour in a steamer, and the resulting steamed soybeans were processed with a chopper into a minced form containing bean pieces. To this was added a rice koji culture in a soybean to rice koji ratio of 1:1, and treatment under applied heat and pressure at 60° C. and 50 MPa was carried out for two days. Evaluation was carried out in the same way as in Working Example 1, as a result of which a taste comparable to that of the comparative miso soup was obtained and the flavor was better than that of the comparative miso soup. Hence, the salt-free miso clearly was perfectly satisfactory as a miso.

Example 7

Water was added to 500 g of soybeans so as to completely immerse them, and the beans were soaked overnight at room temperature (20° C.). The soaked beans were then steamed for one hour in a steamer, and the resulting steamed soybeans were processed with a chopper into a minced form containing bean pieces. To this was added a rice koji culture in a soybean to rice koji ratio of 1:1, and treatment under applied heat and pressure at 50° C. and 80 MPa was carried out for one day. Evaluation was carried out in the same way as in Working Example 1, as a result of which a taste comparable to that of the comparative miso soup was obtained and the flavor was better than that of the comparative miso soup. Hence, the salt-free miso clearly was perfectly satisfactory as a miso.

Comparative Example 1

Water was added to 500 g of soybeans so as to completely immerse them, and the beans were soaked for 24 hours at room temperature (20° C.). The soaked beans were then boiled for four hours and allowed to cool, after which the resulting boiled soybeans were processed in a mixer. To this was added a rice koji culture in a soybean to rice koji ratio of 2:1, and treatment under applied heat and pressure at 50° C. and 60 MPa was carried out for 24 hours. Evaluation was carried out in the same way as in Working Example 1, as a result of which the taste did not differ from that of commercial miso, but a miso flavor was completely absent. This is presumably because the flavor ingredients drained off when the soybeans were boiled.

Comparative Example 2

Water was added to 500 g of soybeans so as to completely immerse them, and the beans were soaked for 24 hours at room temperature (20° C.). The soaked beans were then boiled for four hours and allowed to cool, after which the resulting boiled soybeans were processed in a mixer. To this was added a rice koji culture in a soybean to rice koji ratio of 2:1, and treatment under applied heat and pressure at 50° C. and 60 MPa was carried out for three days. Evaluation was carried out in the same way as in Working Example 1, as a result of which the taste did not differ from that of commercial miso, but a miso flavor was completely absent. This is presumably because the flavor ingredients drained off when the soybeans were boiled.

Trial Example 1

(1) Test Substance
  Salt-free miso obtained in Working Example 7.
(2) Test Animals
  Sixteen 4-week-old male Sprague-Dawley rats (Shimizu Laboratory Supplies Co., Ltd.; Kyoto) were purchased. After a sufficient period of quarantining and acclimatization, the general state of the animals was observed and their body weights measured, following which the animals were used.
(3) Rearing Conditions
  The rearing conditions were set as follows. Temperature: 22±3° C.; humidity: 55±15%; ventilation: constant all-fresh air system; illumination: 12 hours/day (6:00 AM to 6:00 PM). The animals were kept individually in plastic rearing cages.
(4) Feed and Water
  Control Group: Fed ad libitum with a high-fat diet containing 30 wt % beef tallow during period of trial.
  Salt-Free Miso Group: Fed ad libitum with high-fat diet containing 30 wt % beef tallow and 10 wt % salt-free miso during period of trial.
  In both the control group and the salt-free miso group, the water supplied was Fukuyama City tap water which was given freely to the animals with an automatic waterer.
(5) Method of Administration
  After quarantining and acclimatization, the 16 animals were divided into two groups: a control group (8 rats) and a salt-free miso group (8 rats). Ad libitum feeding was continued for six weeks. The animals were fasted for 5 hours before the end of the trial, after which blood was drawn from a vein and the triglyceride (TG), total cholesterol, glucose and GPT levels were measured by Dry Chem (Fujifilm Corporation). Following the end of the trial, the liver was removed and weighed.

Figure 2:
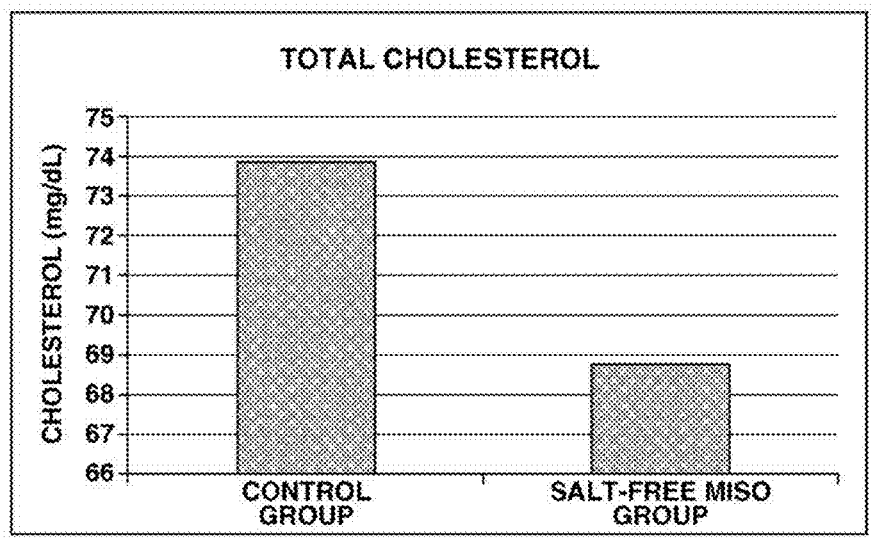
FIG. 2 is a graph showing the total cholesterol results in Trial Example 1.
Figure 3:
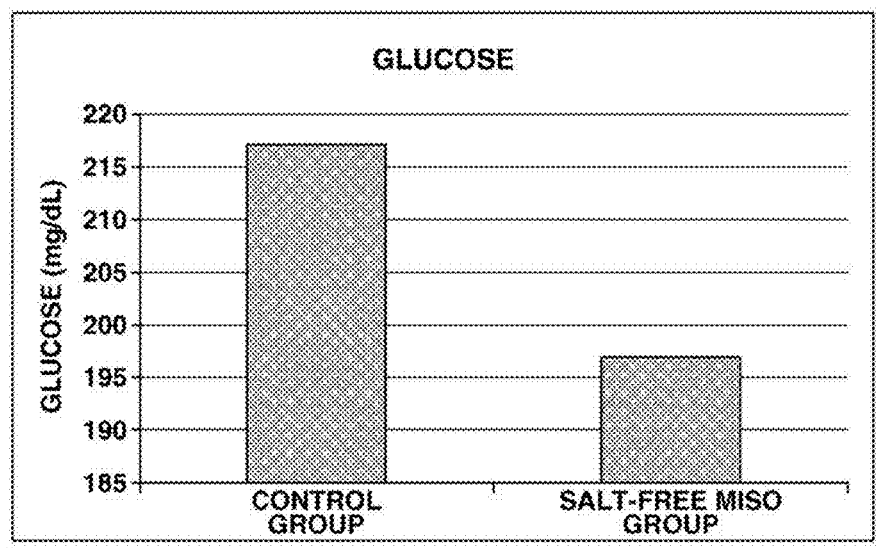
FIG. 3 is a graph showing the glucose results in Trial Example 1.
Figure 4:
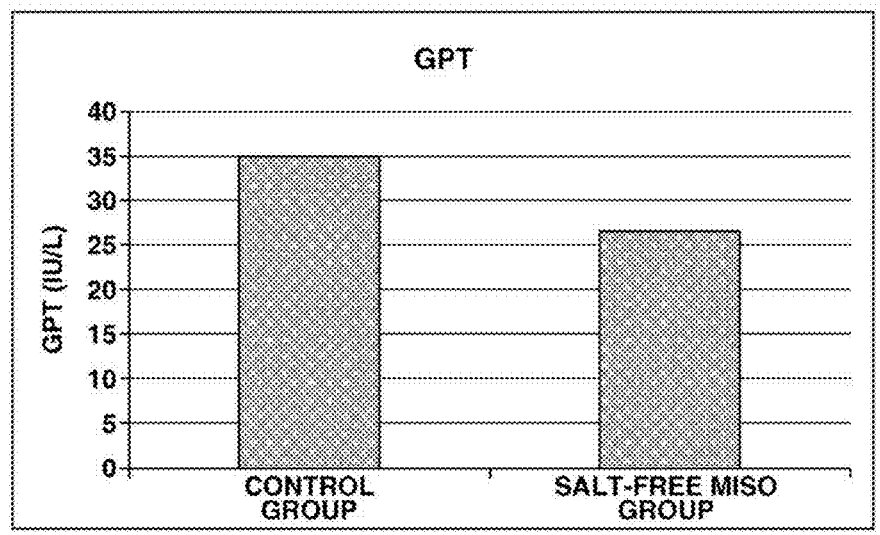
FIG. 4 is a graph showing the GPT results in Trial Example 1.
Figure 5:
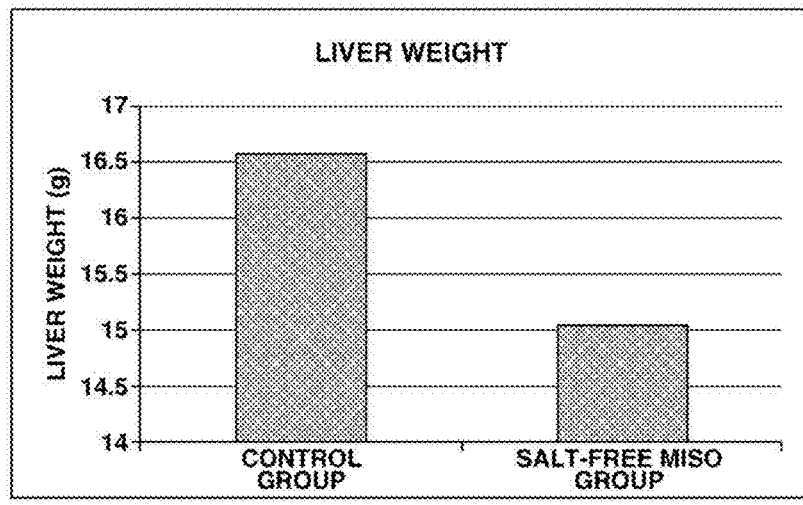
FIG. 5 is a graph showing the liver weight results in Trial Example 1.

The triglyceride (TG), total cholesterol, glucose, GPT and liver weight results are shown in the following figures. FIG. 1: Triglyceride (TG); FIG. 2: Total cholesterol; FIG. 3: Glucose; FIG. 4: GPT; FIG. 5: Liver weight.

Figure 6:
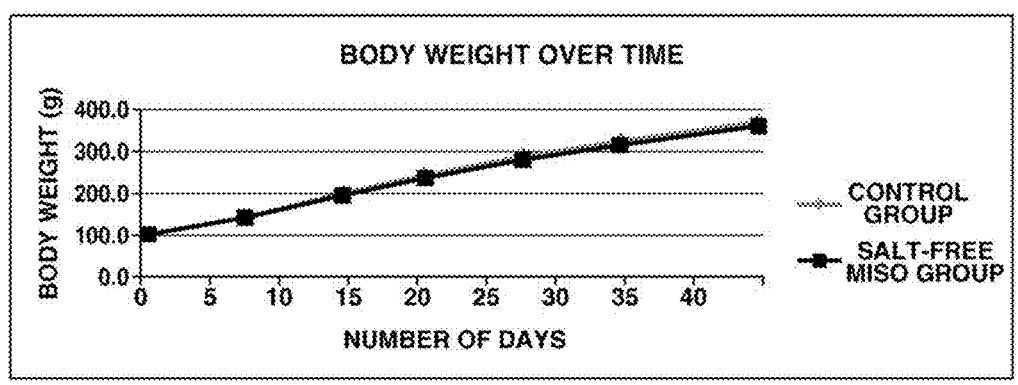
FIG. 6 is a graph showing the change in body weight results in Trial Example 1.

As is apparent from these results, compared with the control group, decreases in triglyceride (TG), total cholesterol, glucose, GPT and liver weight were observed in the group given salt-free miso, confirming a hepatic function-improving effect. Also, the liver weight increased in the control group. However, in spite of the high-fat diet, the liver weight did not change in the salt-free miso group, thus demonstrating a hepatic function-improving effect. FIG. 6 shows the change in body weight over time. Because there was no difference between the control group and salt-free miso group, salt-free miso does not appear to affect growth.

Trial Example 2

(1) Test Substance
  Salt-free miso obtained in Working Example 7.
(2) Test Animals
  Twenty 11-week-old SHR/Izm male rats (Shimizu Laboratory Supplies Co., Ltd.; Kyoto) were purchased. After a sufficient period of quarantining and acclimatization, the general state of the animals was observed and their body weights were measured. Those animals in a good state of health were selected and used at the age of 12 weeks.
(3) Rearing Conditions
  The rearing conditions were set as follows. Temperature: 22±3° C.; humidity: 55±15%; ventilation: constant, all-fresh air system; illumination: 12 hours/day (6:00 AM to 6:00 PM). The animals were held three to a plastic rearing cage.
(4) Feed and Water
  Formula feed having the composition shown in Table 1 below was used. The water supplied to the animals was Fukuyama City tap water which was given freely to each animal with an automatic waterer.

TABLE 1

|  | Control group (wt %) | Salt-free miso group (wt %) |
|---|---|---|
| Casein | 23.0 | 21.5 |
| Corn oil | 10.0 | 8.5 |
| Vitamin mixture | 1.0 | 1.0 |
| Salt mixture | 3.5 | 3.5 |
| Cellulose | 5.0 | 4.0 |
| Sucrose | 18.7 | 18.7 |
| Cornstarch | 37.2 | 31.2 |
| Sodium chloride | 1.0 | 1.0 |
| Cholesterol | 0.5 | 0.5 |
| Sodium cholate | 0.1 | 0.1 |
| Salt-free miso | 0 | 10.0 |

(5) Method of Administration
  After quarantining and acclimatization, the 20 animals were divided into two groups: a control group (10 rats) and a salt-free miso group (10 rats). Ad libitum feeding was continued for 11 weeks. The amounts of feed consumed are indicated below.
(Feed Consumption)
  Limitations were placed on the consumption of feed. The limitations on feed consumption are shown in Table 2 below.

TABLE 2

| Number of days | Amount of feed supplied |
|---|---|
| Days 1 to 2 | 15 g |

TABLE 2-continued

| Number of days | Amount of feed supplied |
|---|---|
| Day 3 | 16 g |
| Days 4 to 5 | 17 g |
| Days 6 to 7 | 18 g |
| Days 8 to 9 | 19 g |
| Days 10 to 30 | 20 g |
| After day 30 | 18 g |

(6) Measurement of Blood Pressure

The blood pressure from the caudal artery was measured using an MK-2000 non-heating, non-invasive blood pressure monitor for rats (Muromachi Kikai Co., Ltd.). Pressure measurements in consecutive administration trials were carried out each Monday before noon. Prior to measurement, the rat immobilizer was warmed and measurement was carried out in a non-stressful state.

Figure 7:
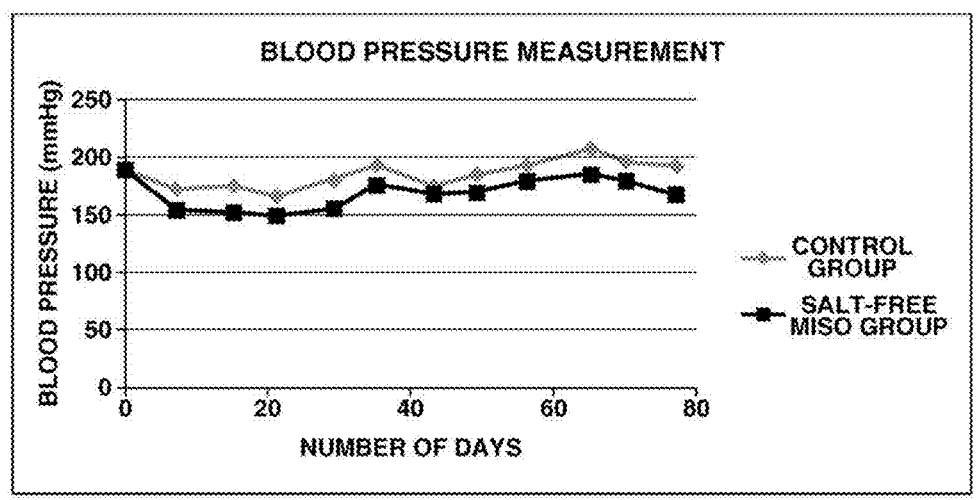
FIG. 7 is a graph showing the results of blood pressure measurements in Trial Example 2.
Figure 8:
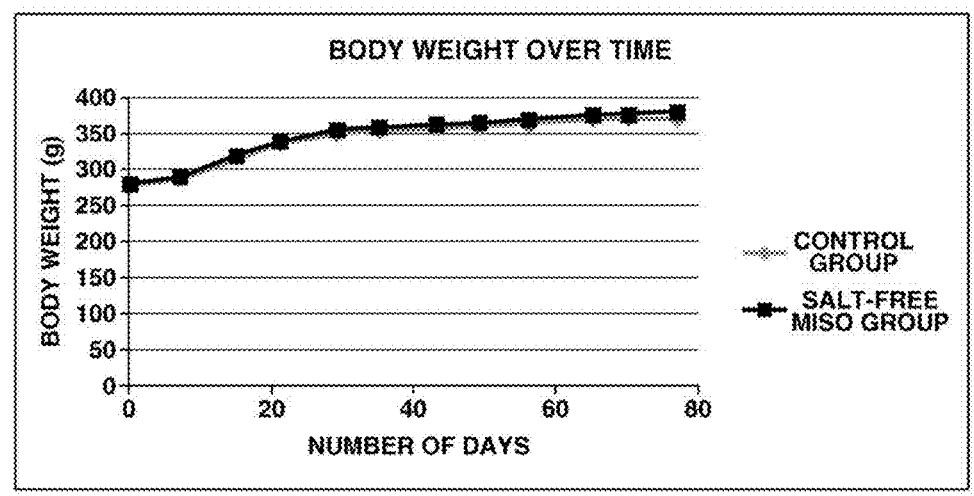
FIG. 8 is a graph showing the change in body weight results in Trial Example 2.

The blood pressure measurement results are shown in FIG. 7. As is apparent from these results, compared with the control group, the salt-free miso group was confirmed to have a lowered blood pressure, demonstrating a hypertension-ameliorating effect. The change in body weight is shown in FIG. 8. Because there was no observable difference in body weight between the control group and the salt-free miso group, salt-free miso does not appear to affect growth. In FIGS. 7 and 8, "0" number of days refers to before administration of the test substance.

The invention claimed is:

1. A method of producing salt-free product of reaction of steamed soybeans with koji culture, comprising the step of fermenting steamed soybeans and koji culture under applied heat and pressure,
    wherein the applied heat and pressure conditions are a pressure of 50 to 80 MPa and a temperature of 50 to 60° C., and
    the length of the fermenting step is one to five days.

* * * * *